United States Patent [19]

Lindner et al.

[11] Patent Number: 5,141,938
[45] Date of Patent: Aug. 25, 1992

[54] PARASITICIDAL SUBSTITUTED 1,2,4-TRIAZINEDIONES

[75] Inventors: Werner Lindner, Cologne; Axel Haberkorn, Wuppertal, both of Fed. Rep. of Germany

[73] Assignee: Bayer Aktiengesellschaft, Leverkusen, Fed. Rep. of Germany

[21] Appl. No.: 696,796

[22] Filed: May 7, 1991

[30] Foreign Application Priority Data

May 17, 1990 [DE] Fed. Rep. of Germany ....... 4015835
Sep. 22, 1990 [DE] Fed. Rep. of Germany ....... 4030042

[51] Int. Cl.$^5$ .................. A01N 43/64; A61K 31/53
[52] U.S. Cl. ................................................ 514/242
[58] Field of Search ........................................ 514/242

[56] References Cited

U.S. PATENT DOCUMENTS

| | | | |
|---|---|---|---|
| 4,640,917 | 2/1987 | Rosner et al. | 514/242 |
| 4,782,056 | 11/1988 | Reiner et al. | 514/242 |
| 4,935,423 | 6/1990 | Lindner et al. | 514/242 |
| 5,070,091 | 12/1991 | Mehlhorn et al. | 514/242 |

FOREIGN PATENT DOCUMENTS

| | | |
|---|---|---|
| 170,136 | 2/1986 | European Pat. Off. |
| 330,041 | 8/1989 | European Pat. Off. |
| 353,526 | 2/1990 | European Pat. Off. |
| 377,903 | 7/1990 | European Pat. Off. |
| 377,904 | 7/1990 | European Pat. Off. |
| 2,532,363 | 2/1977 | Fed. Rep. of Germany. |
| 3261783 | 11/1991 | Japan. |

Primary Examiner—Allen J. Robinson
Attorney, Agent, or Firm—Sprung, Horn, Kramer & Woods

[57] ABSTRACT

A method of combating parasitic protozoa which comprises applying thereto an amount effective therefor of a 1,2,4-triazinedione of the formula

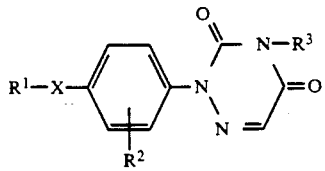

in which
$R^1$ represents optionally substituted pyridyl, pyrazinyl or pyrimidinyl,
X represents O, S, SO, SO$_2$ or —CR$^4$(CN)—,
$R^2$ represents hydrogen, one or more, identical or different radicals of the group comprising hydrogen, halogen, nitro, alkyl, alkoxy, alkylthio, halogenoalkyl, halogenoalkoxy, alkylthio and halogenoalkylthio,
$R^3$ represents hydrogen, optionally substituted alkyl, alkenyl, alkinyl or aralkyl, and
$R^4$ represents hydrogen or alkyl.

4 Claims, No Drawings

PARASITICIDAL SUBSTITUTED 1,2,4-TRIAZINEDIONES

The present invention relates to the use of substituted 1,2,4-triazinediones as agents for combating parasitic protozoa and in particular coccidia as well as fish and insect parasites.

The use of certain substituted 1,2,4-triazinediones for combating coccidia is known. However, the action of these compounds is not satisfactory in every case.

It has been found that the substituted 1,2,4-triazinediones of the general formula

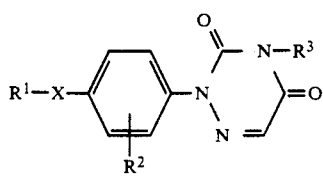

in which
- $R^1$ represents optionally substituted pyridyl, pyrazinyl or pyrimidinyl,
- X represents O, S, SO, $SO_2$ or $-CR^4(CN)-$,
- $R^2$ represents one or more identical or different radicals of the group comprising hydrogen, halogen, nitro, alkyl, alkoxy, alkylthio, halogenoalkyl, halogenoalkoxy, alkylthio and halogenoalkylthio,
- $R^3$ represents hydrogen, optionally substituted alkyl, alkenyl, alkinyl or aralkyl and
- $R^4$ represents hydrogen or alkyl, are outstandingly suitable for combating parasitic protozoa.

The compounds of the formula I are the subject of a pending application Ser. No. 459,895, filed Jan. 2, 1990, corresponding to DE-OS (German Published Specification) 3,900,373. They are used there for the preparation of the corresponding hydrogenated compounds.

Substituted 1,2,4-triazinediones of the general formula

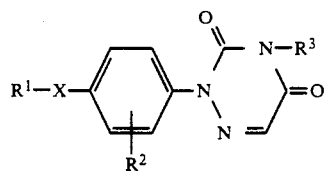

in which $R^1$, $R^2$ and $R^3$ have the abovementioned meanings, can be prepared by a process in which a) compounds of the formula Ia

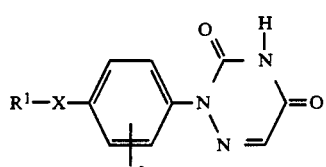

in which X, $R^1$ and $R^2$ have the abovementioned meanings, are reacted with compounds of the formula II $$R^3\text{—B} \quad \text{II}$$

in which $R^3$ has the abovementioned meanings and
B represents halogen, $OSO_2$-alkyl, $-OSO_2-$aryl, or $-O-SO_2$-halogenoalkyl, or in which compounds of the formula III

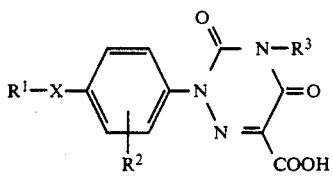

in which X, $R^1$, $R^2$ and $R^3$ have the abovementioned meanings, are decarboxylated by heating or c) in which compounds of the formula IV

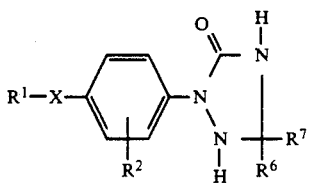

in which
- X represents O, S, $-CR^4(CN)-$,
- $R^1$ and $R^2$ have the abovementioned meanings,
- $R^4$ is hydrogen or alkyl and
- $R^6$ and $R^7$ represent optionally substituted alkyl, are reacted with glyoxylic acid of the formula X $$\text{CHO—COOH} \quad \text{X}$$

in the presence of inorganic or organic acids, or d) in which compounds of the formula V

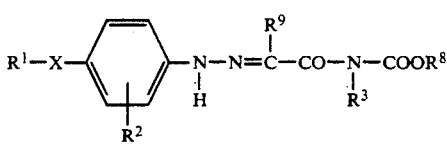

in which
- X represents O, S or $-CR^4(CN)-$,
- $R^1$, $R^2$, $R^3$ and $R^4$ have the abovementioned meanings,
- $R^8$ represents alkyl or optionally substituted aryl, and
- $R^9$ represents H, are heated in the presence of bases, or e) in which compounds of the formula VI

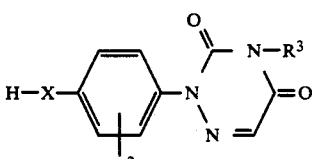

in which
- X represents O or S, and
- $R^2$ and $R^3$ have the abovementioned meanings, are reacted with compounds of the formula VII $$R^1\text{—A} \quad \text{VII}$$

in which

R¹ has the abovementioned meaning and

A represents the radicals halogen, O—SO₂-alkyl, —O—SO₂-halogenoalkyl, O—SO₂-aryl, —S-alkyl, —SO₂-alkyl or SO₂-halogenoalkyl.

Some of the compounds of the formulae VII, IV, V and VI are known from pending application Ser. No. 310,809, filed Jun. 19, 1990, corresponding to DOS (German Published Specification) 3,805,660 or are the subject of application Ser. No. 459,895, supra.

Preferably used compounds of the formula I are compounds
in which

R¹ represents pyrimidinyl, pyridinyl and pyrazinyl which are optionally substituted by halogen, alkyl, cyano, nitro, alkoxy, alkylthio, halogenoalkyl, halogenoalkoxy, halogenoalkylthio, halogenoalkylsulphonyl, halogenoalkylsulphinyl, amino, alkylamino, halogenoalkylamino or acylamino, X represents O, S or —CH(CN)—, R² represents halogen or $C_{1-6}$-alkyl:, and R³ represents hydrogen or $C_1$–$C_4$-alkyl, in particular methyl.

Particularly preferred compounds of the formula I are those
in which

X represents O or —CH(CN)—,

R represents pyridinyl or pyrimidinyl which are optionally substituted by $C_{1-4}$-alkyl, in particular methyl, $C_{1-4}$-halogenoalkyl, in particular trifluoromethyl, halogen, in particular chlorine, bromine or fluorine, nitro, CN, $C_{1-4}$-alkoxy, in particular methoxy, $C_{1-4}$-halogenoalkoxy, in particular trifluoromethoxy, $C_{1-4}$alkylthio, in particular methylthio, $C_{1-4}$-halogenoalkylthio, in particular trifluoromethylthio, $C_{1-4}$-halogenoalkylsulphonyl, in particulartrifluoromethylsulphonyl, $C_{1-4}$-halogenoalkylsulphinyl, in particular trifluoromethylsulphinyl, amino,$C_{1-4}$-alkylamino,$C_{1-4}$-halogenoalkylamino or acylamino, in particular acetylamino, R² represents one or more radicals from the group comprising hydrogen or halogen, in particular chloride or bromine, $C_{1-4}$-alkyl, in particular methyl, or 1–5-halogeno($C_{1-4}$)-alkyl, in particular trifluoromethyl, and R³ represents hydrogen or methyl.

Very particularly preferred compounds of the formula I are those
in which

X represents O or CH(CN),

R¹ represents pyridinyl which is optionally substituted by nitro, chlorine, methyl or trifluoromethyl, R² represents one or more radicals from the group comprising hydrogen, methyl and chlorine, and R³ represents hydrogen or methyl.

Individual compounds which may be mentioned are:

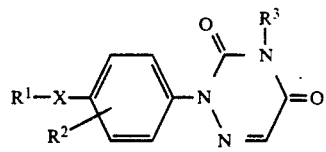

| R¹ | X | R² | R³ |
|---|---|---|---|
| 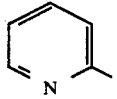 | CHCN | 3,5-Cl₂ | H |
| 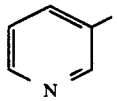 | CHCN | 3,5-Cl₂ | H |
| 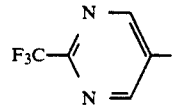 | O | 3,5-Cl₂ | H |
| 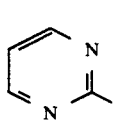 | O | 3,5-Cl₂ | H |
| 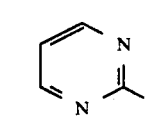 | O | 3,5-(CH₃)₂ | H |
| 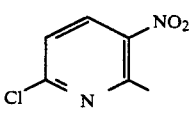 | O | 3,5-Cl₂ | H |
| 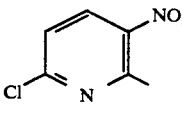 | O | 3,5-(CH₃)₂ | H |
| 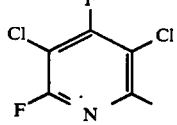 | O | 3,5-Cl₂ | H |
| 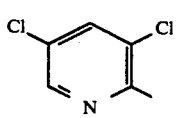 | O | 3,5-Cl₂ | H |
| 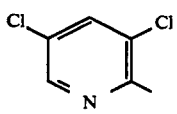 | O | 3,5-(CH₃)₂ | H |
| 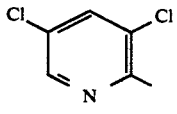 | O | 3,5-(CH₃)₂ | H |

-continued

| | R¹ | X | R² | R³ |
|---|---|---|---|---|
| | 3,5-dinitro-2-methylpyridin-6-yl (O₂N, NO₂ on pyridine with N) | O | 3,5-Cl₂ | H |
| | 3-chloro-2-methylpyridin-6-yl | O | 3,5-Cl₂ | H |
| | 4-methyl-5-nitro-2-methylpyridin-6-yl (O₂N, CH₃) | O | 3,5-Cl₂ | H |
| | 4-methyl-5-nitro-2-methylpyridin-6-yl (O₂N, CH₃) | O | 3,5-(CH₃)₂ | H |
| | 2,6-dimethylpyridin-... (H₃C-pyridine) | O | 3,5-Cl₂ | H |
| | 6-chloro-2-methylpyridin-... (Cl-pyridine) | O | 3,5-Cl₂ | H |
| | 6-chloro-2-methylpyridin-... (Cl-pyridine) | O | 3,5-(CH₃)₂ | H |
| | 6-trifluoromethyl-2-methylpyridin-... (F₃C-pyridine) | O | 3,5-Cl₂ | H |
| | 6-trifluoromethyl-2-methylpyridin-... (F₃C-pyridine) | O | 3,5-(CH₃)₂ | H |
| | 6-trifluoromethyl-2-methylpyridin-... (F₃C-pyridine) | O | 3,5-(CH₃)₂ | H |
| | pyrazinyl (N,N) | O | 3,5-Cl₂ | H |

The processes described in the following are the subject of application Ser. No. 459,895, supra.

If 2-[4-(2,-pyridyloxy)phenyl]-1,2,4-triazine-3,5-(2H,4H)dione is employed as the compound of the formula Ia and methyl iodide is employed as the compound of the formula II in process a) for the preparation of the compounds of the formula II in which R³ does not represent hydrogen, the process can be described by the following equation:

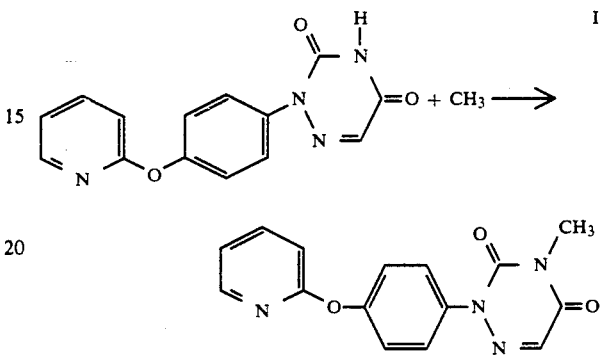

The compounds of the formula Ia are prepared as described in process b).

The compounds of the formula II are known or can be prepared by known methods. Methyl iodide and ethyl bromide may particularly be mentioned.

The process is carried out by reacting a compound of the formula Ia with compounds of the formula II in the presence of a base and of a diluent.

Suitable diluents in this case are virtually all the inert organic solvents. These preferably include aliphatic and aromatic, optionally halogenated hydrocarbons, benzine, ligroin, benzene, toluene, xylene, methylene chloride, ethylenechloride, chlorobenzene and o-dichlorobenzene, ethers such as diethyl ether and dibutyl ether, glycol dimethyl ether and diglycol dimethyl ether, tetrahydrofuran and dioxane, ketones such as acetone, methyl ethyl ketone, methyl isopropyl ketone and methyl isobutyl ketone, esters such as methyl acetate and ethyl acetate, nitriles such as, for example, acetonitrile and propionitrile, amides such as, for example, dimethylformamide, dimethylacetamide and N-methylpyrrolidone and also dimethyl sulphoxide, tetramethylenesulphone and hexamethylphosphoric triamide.

The process is carried out in the presence of bases. Preferred bases which may be mentioned are the alkali metal hydroxides such as sodium hydroxide, alkali metal alkoxides such as sodium methoxide or potassium butoxide, metal hydrides such as sodium hydride or organic bases such as 1,8-diazabicyclo[5.40]-undec-7-ene (DBU).

The process is carried out at normal pressure and at temperatures between 20° and 140° C.

The reaction is carried out by combining equimolar amounts of the compound of the formula Ia and base, adding an equimolar amount of the compound of the formula II to this mixture and heating to the reaction temperature.

Both the compounds of the formula I and the compounds of the formula Ia can be prepared by process Ib), now described.

If 2-(3-methyl-4-pyridylphenyl)-1,2,4-triazine-2,5-(2H,4H)dione-6-carboxylic acid is employed as the compound of the formula III in process Ib) for the preparation of the compounds of the formula I, the process can be described by the following equation:

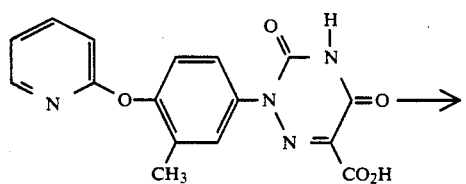

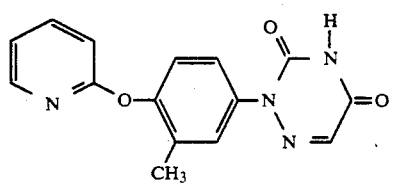

The compounds of the formula III are the subject of the already mentioned applications hereinabove. Compounds of the formula III are preferably employed in which X, $R^1$, $R^2$ and $R^3$ have the preferred meanings indicated for the compounds of the formula I.

Individual compounds of the formula III which may be mentioned are:

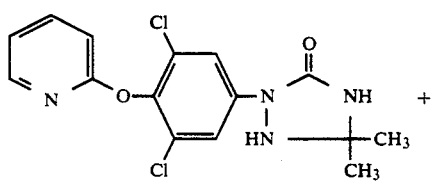

| $R^1$ | X | $R^2$ | $R^3$ |
|---|---|---|---|
|  (pyridyl) | CH(CN) | 3,5-Cl$_2$ | H |
| " | O | 3,5-Cl$_2$ | H |
| " | O | 3-CH$_3$ | H |
| F$_3$C-pyridyl | O | 3,5-Cl$_2$ | H |
| pyrimidinyl | O | 3,5-Cl$_2$ | H |
| pyridyl | CH(CN) | 3,5-Cl$_2$ | H |

The decarboxylation is optionally carried out in the presence of inert organic diluents. These include aliphatic and aromatic, optionally halogenated hydrocarbons such as nonane, decane, dodecane, xylenes, alcohols such as diethylene glycol, ethers such as ethylene glycol monobutyl ether and diethylene glycol dibutyl ether, sulphoxides such as dimethyl sulphoxide and sulphones such as tetramethylenesulphone.

Moreover, the reaction can be carried out in the presence of mercapto group-containing carboxylic acids such as, for example, mercaptoacetic acid or thiosalicylic acid.

The reaction is carried out at temperatures between 150° and 300° C., optionally in the presence of mercapto group-containing carboxylic acids such as, for example, mercaptoacetic acid, preferably between 160° and 250° C., in particular between 180° and 210° C.

The reaction is carried out at normal pressure. The compounds of the formulae III are heated in substance or dissolved or suspended in the respective diluent.

If 1-[3,5-dichloro-4-(2-pyridyl)-phenyl]-3,3-dimethyl-1,2,4-triazolidin-5-one is employed as the compound of the formula IV in process Ic) for the preparation of the compounds of the formula I, the process can be described by the following equation:

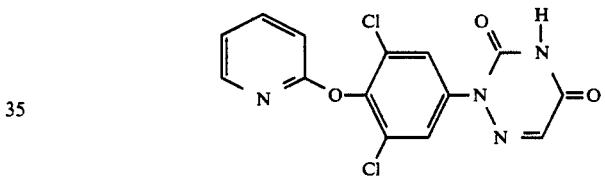

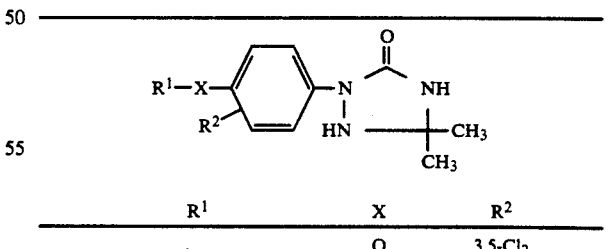

The compounds of the formula IX are new. Their preparation is the subject of the already mentioned application, supra.

Preferably, compounds of the formula IV are employed in which X, $R^1$ and $R^2$ have the preferred meanings indicated for the compounds of the formula I and $R^6$ and $R^7$ independently of one another represent $C_{1-4}$-alkyl, in particular methyl or ethyl. The following may be mentioned in particular:

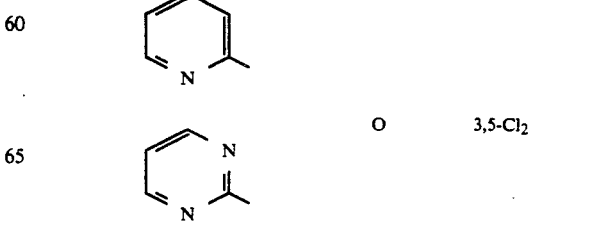

| $R^1$ | X | $R^2$ |
|---|---|---|
| pyridyl | O | 3,5-Cl$_2$ |
| pyrimidinyl | O | 3,5-Cl$_2$ |

-continued

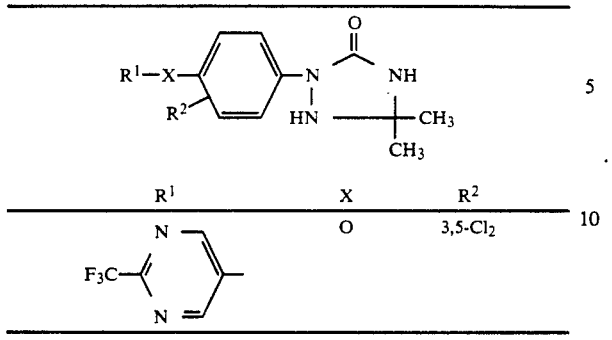

| $R^1$ | X | $R^2$ |
|---|---|---|
| F₃C-⟨pyridine⟩- | O | 3,5-Cl₂ |

The process is carried out by heating a compound of the formula IV in a diluent in the presence of glyoxylic acid and a catalytic amount of concentrated mineral acid and chromatographing the crude product on silica gel after aqueous work-up.

Diluents which can be used are all inert organic solvents which have been mentioned, for example, for process Ia). Sulphuric acid is preferably used as the mineral acid. The reaction is carried out at temperatures between 60° C. and 130° C., preferably at 100° C.

If ethyl N-[[3-methyl-4-(5,-trifluoromethyl-2'-pyridinyloxyphenyl]hydrazinylidene-carbonyl]carbamate is employed as the compound of the formula V in process d) for the preparation of the compounds of the formula I, the process can be described by the following equation:

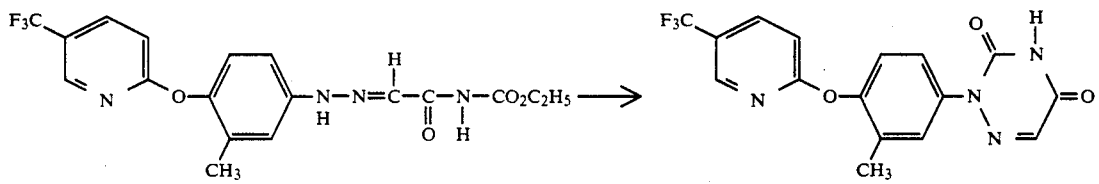

The compounds of the formula V are new. Their preparation is the subject of the already mentioned unpublished application, supra.

Preferably, compounds of the formula V are employed in which X, $R^1$, $R^2$ and $R^3$ have the preferred meanings indicated for the compounds of the formula I, $R^8$ represents $C_{1-4}$-alkyl, in particular methyl or ethyl and phenyl and $R^9$ represents hydrogen or CN.

Individual compounds of the formula V which may be mentioned are:

$R^1-X-\langle\text{phenyl}(R^2)\rangle-N(H)-N=C(R^9)-C(=O)-N(H)-COOR^6$

| $R^1$ | X | $R^2$ | $R^4$ | $R^6$ |
|---|---|---|---|---|
| ⟨2-pyridinyl⟩ | CHCN | 3,5-Cl₂ | H | Et |
| ⟨2-pyridinyl⟩ | O | 3,5-Cl₂ | H | Et |
| ⟨2-pyridinyl⟩ | O | 3-CH₃ | H | Et |

-continued $R^1-X-\langle\text{phenyl}(R^2)\rangle-N(H)-N=C(R^9)-C(=O)-N(H)-COOR^6$

| $R^1$ | X | $R^2$ | $R^4$ | $R^6$ |
|---|---|---|---|---|
| F₃C-⟨pyridinyl⟩- | O | 3,5-Cl₂ | H | Et |
| ⟨3-pyridinyl⟩ | CHCN | 3,5-Cl₂ | H | Et |

The process is carried out by heating a compound of the formula V, if desired in the presence of a solvent and of a base.

Solvents and bases used are the solvents and bases mentioned in process a) for the preparation of the compounds I. Other particularly preferred organic solvents which are employed are alcohols such as, for example, ethanol or organic acids such as, for example, glacial acetic acid.

Particularly preferred bases are the hydroxides and acetates of the alkali metals or alkaline earth metals such as, for example, NaOH or sodium acetate and potassium acetate.

The reaction is carried out under normal pressure at temperatures between 70° and 150° C., preferably between 70° and 100° C.

The base used is employed in a 10–80% molar excess. The reaction mixture is preferably acidified with a dilute mineral acid such as, for example, hydrochloric acid after completion of the cyclization and the product obtained as a solid is filtered off.

If 2-(3,5-dichloro-4-hydroxyphenyl)-1,2,4-triazine-3,5(2H,4H)dione is employed as the compound VI and 2-chloropyridine is employed as the compound of the formula VII in process Ie) the process can be described by the following equation.

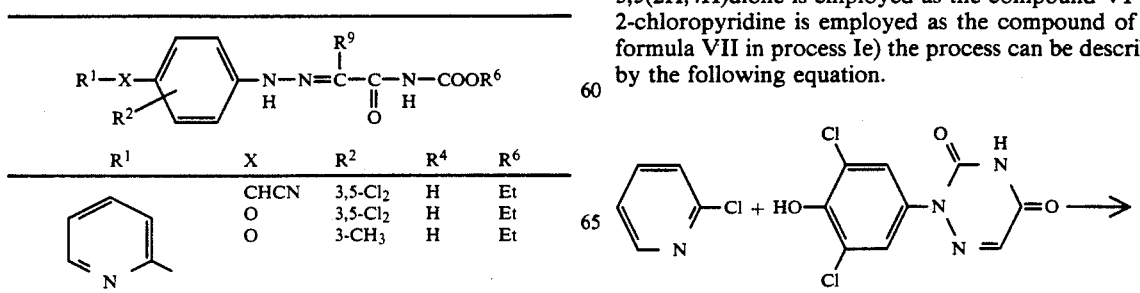

-continued

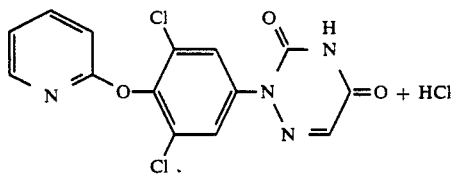

Compounds of the formula VI in which $R^2$ and $R^3$ represent hydrogen, are known (J. Slouka, Acta Unio Palacki Olomuk. Fac. Rerum. Nat. 1984 (Chem 23), 39–45; C.A. 102 203946c).

Other compounds of the formula VI are the subject of a hitherto unpublished application by the Applicant (German Patent Application P 3,805,660). They can be prepared analogously to the process indicated for the compounds of the formula I.

Compounds of the formula VI may preferably be mentioned in which $R^2$ and $R^3$ have the preferred meanings mentioned for the compounds of the formula I.

The substituted heterocycles of the formula VII are known or can be prepared analogously to known processes (Beilstein Vol. 20. p. 230, 20, 1st Suppl. p. 82, 20, p. 359; Katrizky and Rees, Comprehensive Het. Chem. Col. 6 1984).

They have the preferred meanings indicated above for the compounds of the formula I. The following compounds of the formula VII may be mentioned in particular:

VII

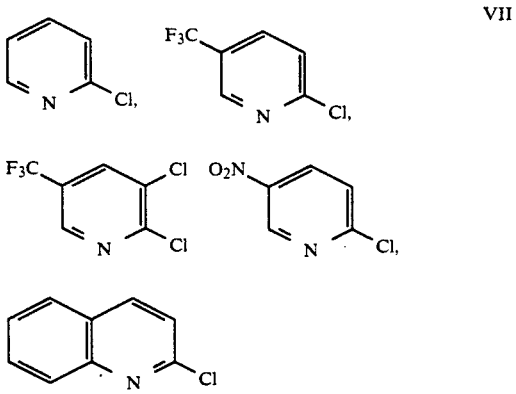

The reaction is preferably carried out using diluents.

Suitable diluents in this case are virtually all the inert organic solvents. These preferably include aliphatic and aromatic, optionally halogenated hydrocarbons, benzine, ligroin, benzene, toluene, xylene, methylene chloride, ethylene chloride, chloroform, carbon tetrachloride, chlorobenzene and o-dichlorobenzene, ethers such as diethyl ether and dibutyl ether, glycol dimethyl ether and diglycol dimethyl ether, tetrahydrofuran and dioxane, ketones such as acetone, methyl ethyl ketone, methyl isopropyl ketone and methyl isobutyl ketone, esters such as methyl acetate and ethyl acetate, nitriles such as, for example, acetonitrile and propionitrile, amides such as, for example, dimethylformamide, dimethylacetamide and N-methyl-pyrrolidone and also dimethyl sulphoxide, tetramethylenesulphone and hexamethylphosphoric triamide.

The reaction is carried out in the presence of inorganic or organic acid acceptors.

Examples of those which may be mentioned are: alkali metal hydroxides such as, for example, sodium hydroxide and potassium hydroxide, alkaline earth metal hydroxides such as, for example, calcium hydroxide, alkali metal carbonates and alkoxides such as sodium carbonate and potassium carbonate, sodium methoxide and sodium ethoxide or potassium methoxide and potassium ethoxide, and in addition aliphatic, aromatic or heterocyclic amines, for example triethylamine, pyridine, 1,5-diazabicyclo-[4.3.0]-non-5-ene (DBN), 1,8-diazabicyclole-[5.4.0]-undec-7-ene (DBU) and 1,4-diazabicyclole [2.2.2]-octane (DABCO).

The reaction is carried out at temperatures between 50° and 200° C., preferably between 80 and 160° C. at normal pressure or elevated pressure. It is preferably carried out at normal pressure.

The process is carried out by combining equimolar amounts of the compounds of the formula XVII and XVIII in one of the diluents indicated and heating. After reaction is complete, the reaction mixture is acidified with dilute inorganic acid (for example hydrochloric acid) and the resulting precipitate is filtered off, washed and dried.

The active compounds are suitable for combating parasitic protozoa of man and animals which are encountered in the keeping and raising of animals in the case of productive, breeding, zoo, laboratory, experimental and pet animals, and have favorable toxicity to warm-blooded animals. They are active against all or individual stages of development of the pests and against resistant and normally sensitive strains. By combating the parasitic protozoa, disease, cases of death and yield reductions (for example in the production of meat, milk, wool, hides, eggs, honey, etc.) should be reduced so that more economical and simpler keeping of animals is possible through the use of the active compounds.

The parasitic protozoa include:

Mastigophora (Flagellata) such as, for example, Trypano-somatidae, for example *Trypanosoma b. brucei, T.b. gambiense, T.b. rhodesiense, T. congolense, T. cruzi, T. evansi, T. equinum, T. lewisi, T. percae, T. simiae, T. vivax, Leishmania brasiliensis, L. donovani, L. tropica*, such as, for example, Trichomonadidae, for example *Giardia lamblia* and *G. canis*.

Sarcomastigophora (Rhizopoda) such as Entamoebidae, for example *Entamoeba histolytica*, Hartmanellidae, for example Acanthamoeba sp. and Hartmanella sp.

Apicomplexa (Sporozoa) such as Eimeridae, for example *Eimeria acervulina, E. adenoides, E. alabahmensis, E. anatis, E. anseris, E. arloingi, E. ashata, E. auburnensis, E.bovis, E. brunetti, E. canis, E. chinchillae, E. clupearum, E. columbae, E. contorta, E. crandalis, E. debliecki, E. dispersa, E. ellipsoidales, E. falciformis, E faurei, E. flavescens, E. gallopavonis, E. hagani, E. intestinalis E. irresidua, E. labbeana, E. leucarti, E. magna, E. maxima, E. media, E.meleagridis, E. meleagrimitis, E. mitis, E. necatrix, E. ninakohlyakimovae, E. ovis, E. ovinodales, E. parva, E. pavonis, E. perforans, E. phasani, E. piriformis, E. praecox, E. residualis, E. scabra, E. spec., E. stiedai, E. suis, E. tenella, E. truncata, E. truttae, E. zuernii, Globidium spec., Isospora belli, I. canis, I. felis, I. ohioensis, I. rivolta, I. spec., I. suis, Cystisospora spec., Cryptosporidium spec.* such as Toxoplasmadidae, for example *Toxoplasma gondii*, such as Sarcocystidae, for example *Saercocystis bovicanis, S. bovihominis, S. ovicanis, S. ovifelis, S. spec., S. suihominis* such as Leucozytoz for example *Leucozytozoon simondi*, such as Plasmodiidae, for example *Plasmodium berghei, P. falcipa-*

*rum, P. malariae, P. ovale, P. vivax, P. spec.*, such as Piroplasmea, for example *Babesia argentina, B. bigemina, B. bovis, B. canis, B. spec., Theileria parva, Theileria spec.*, such as Adeleina, for example *Hepatozoon canis, H. spec.* In addition *Myxosporidia* and *Microspora* for example *Glugea spec.* and *Nosema spec.*

In addition *Pneumocystis carinii* and Ciliophora (Ciliata) such as, for example, *Balantidium coli, Ichthiophthirius* spec., *Trichodina spec.* and *Epistylis spec.*

The compounds according to the invention are also active against protozoa which occur as parasites in insects. Those which may be mentioned are parasites of the Microsporidia strain, in particular the genus Nosema. Particular mention may be made of *Nosema apis* in the honeybee.

The productive and breeding animals include mammals such as, for example, cattle, horses, sheep, pigs, goats, camels, water buffalo, donkeys, rabbits, fallow deer, reindeer, animals having a valuable coat such as, for example, mink, chinchilla, racoons, birds such as, for example, hens, geese, turkeys, ducks, doves, and species of birds for keeping at home and in the zoo. In addition, and ornamental fish are included.

The laboratory and experimental animals include mice, rats, guinea pigs, golden hamsters, dogs and cats.

The pet animals include dogs and cats.

The fish include productive, breeding, aquarium and ornamental fish of all ages which live in fresh and salt water. The productive and breeding fish include, for example, carp, eel, trout, white fish, salmon, bream, roach, rudd, chub, sole, plaice, halibut, Japanese yellowtail (*Seriola quinqueradiata*), Japanese eel (*Anguilla japonica*), red seabream (*Pagurus major*), sea bass (*Dicentrarchus labrax*), grey mullet (*Mugilus cephalus*), pompano, gilthread seabream (*Sparus auratus*), Tilapia spp., chichlidae species such as, for example, Plagioscion or channel catfish. The agents according to the invention are particularly suitable for the treatment of fry, for example carp of 2–4 cm body length. The agents are also very highly suitable in the feeding of eels.

Administration can be carried out both prophylactically and therapeutically.

The administration of the active compounds is carried out directly or enterally, parenterally, dermally or nasally in the form of suitable preparations.

Enteral administration of the active compounds is carried out, for example, orally in the form of powders, suppositories, tablets, capsules, pastes, drinks, granules, drenches, boli, medicated feed or drinking water. Dermal administration can be carried out, for example, in the form of dipping, spraying, bathing, washing, pouring-on and spotting-on and powdering. Parenteral administration is carried out, for example, in the form of injection (intramuscular, subcutaneous, intravenous, intraperitoneal) or by implants.

Suitable preparations are: solutions such as injection solutions, oral solutions, concentrates for oral administration after dilution, solutions for use on the skin or in body cavities, pouring-on formulations and gels;

emulsions and suspensions for oral or dermal administration and also for injection; semi-solid preparations;

formulations in which the active compound is processed in an ointment base or in an oil-in-water or water-in-oil emulsion base;

solid preparations such as powders, premixes or concentrates, granules, pellets, tablets, boli, capsules; aerosols and inhalants, and molded articles containing active compound.

Injection solutions are administered intravenously, intramuscularly and subcutaneously.

Injection solutions are produced by dissolving the active compound in a suitable solvent and, if necessary, adding additives such as solubilizers, acids, bases, buffer salts, antioxidants and preservatives. The solutions are sterile filtered and bottled.

Solvents which may be mentioned are: physiologically tolerable solvents such as water, alcohols such as ethanol, butanol, benzyl alcohol, glycerol, hydrocarbons, propylene glycol, polyethylene glycols, N-methylpyrrolidone, and mixtures of these.

The active compounds may optionally also be dissolved in physiologically tolerable vegetable or synthetic oils which are suitable for injection.

Solubilizers which may be mentioned are: solvents which promote the solution of the active compound in the main solvent or prevent its precipitation. Examples are polyvinylpyrrolidone, polyoxyethylated castor oil and polyoxyethylated sorbitan esters.

Preservatives are: benzyl alcohol, trichlorobutanol, p-hydroxybenzoic acid esters and n-butanol.

Oral solutions are administered directly. Concentrates are administered orally after previously diluting to the administration concentration. Oral solutions and concentrates are prepared as described above for the injection solutions, it being possible to dispense with sterile working.

Solutions for use on the skin are applied dropwise, spread on, rubbed in, sprinkled on, sprayed on or applied by dipping, bathing or washing. These solutions are prepared as described above for the injection solutions.

It may be advantageous to add thickeners during the preparation. Thickeners are: inorganic thickeners such as bentonites, colloidal silica, aluminum monostearate, organic thickeners such as cellulose derivatives, polyvinyl alcohols and their copolymers, acrylates and methacrylates.

Gels are applied to or spread on the skin or introduced into body cavities. Gels are prepared by adding such a quantity of thickener to solutions which have been prepared as described for the injection solutions that a consistency clear composition having an ointment-like consistency results. The thickeners indicated above are employed as thickeners.

Pouring-on formulations are poured onto or sprinkled onto limited areas of the skin, whereupon the active compound either penetrates the skin and acts systemically or is distributed on the body surface.

Pouring-on formulations are prepared by dissolving, suspending or emulsifying the active compound in suitable skin-compatible solvents or solvent mixtures. If appropriate, further auxiliaries such as colorants, absorption-promoting substances, antioxidants, light screens and adhesives are added.

Solvents which may be mentioned are: water, alkanols, glycols, polyethylene glycols, polypropylene glycols, glycerol, aromatic alcohols such as benzyl alcohol, phenylethanol, phenoxyethanol, esters such as ethyl acetate, butyl acetate and benzyl benzoate, ethers such as alkylene glycol alkyl ethers such as dipropylene glycol monomethyl ether and diethylene glycol monobutyl ether, ketones such as acetone and methyl ethyl ketone, aromatic and/or aliphatic hydrocarbons, vegetable or synthetic oils, DMF, dimethylacetamide, N- methylpyrrolidone and 2-dimethyl-4-hydroxy-methylene-1,3-dioxolane.

Colorants are all colorants which may be dissolved or suspended and which are permitted for administration to animals.

Absorption-promoting substances are, for example, DMSO, spreading oils such as isopropyl myristate, dipropylene glycol pelargonate, silicone oils, fatty acid esters, triglycerides and fatty alcohols.

Antioxidants are sulphites or metabisulphites such as potassium metabisulphite, ascorbic acid, butylhydroxytoluene, butylhydroxyanisole and tocopherol.

Light screens are, for example, substances of the benzophenone class or novantisolic acid.

Adhesives are, for example, cellulose derivatives, starch derivatives, polyacrylates, and natural polymers such as alginates and gelatin.

Emulsions may be administered orally, dermally or as injections.

Emulsions are either of the water-in-oil type or the oil-in-water type.

They are prepared by dissolving the active compound either in the hydrophobic or in the hydrophilic phase and homogenizing this with the solvent of the other phase with the aid of suitable emulsifiers and, if appropriate, further auxiliaries such as colorants, absorption-promoting substances, preservatives, antioxidants, light screens and viscosity-increasing substances.

Hydrophobic phases (oils) which may be mentioned are: paraffin oils, silicone oils, natural vegetable oils such as sesame oil, almond oil, castor oil, synthetic triglycerides such as caprylic/capric acid biglyceride, triglyceride mixture with vegetable fatty acids of chain length $C_{8-12}$ or other specially selected natural fatty acids, partial glyceride mixtures of saturated or unsaturated fatty acids possibly also containing hydroxyl groups, and mono- and diglycerides of $C_8/C_{10}$-fatty acids.

Fatty acid esters such as ethyl stearate, di-n-butyryl adipate, hexyl laurate, dipropylene glycol pelargonate, esters of a branched fatty acid of medium chain length containing saturated fatty alcohols of chain length $C_{16}$–$C_{18}$, isopropyl myristate, isopropyl palmitate, caprylic/capric acid esters of saturated fatty alcohols of chain length $C_{12}$–$C_{18}$, isopropyl stearate, oleyl oleate, decyl oleate, ethyl oleate, ethyl lactate, waxy fatty acid esters suoh as dibutyl phthalate, diisopropyl adipate, ester mixtures related to the latter, inter alia ±atty alcohols such as isotridecyl alcohol, 2-octyldodecanol, cetyl stearyl alcohol and oleyl alcohol.

Fatty acids such as, for example, oleic acid and its mixtures.

Hydrophilic phases which may be mentioned are: water, alcohols such as, for example, propylene glycol, glycerol, sorbitol and their mixtures.

Emulsifiers which may be mentioned are: non-ionic surfactants, for example polyoxyethylated castor oil, polyoxyethylated sorbitan monooleate, sorbitan monostearate, glycerol monostearate, polyoxyethyl stearate and alkylphenol polyglycol ethers;

ampholytic surfactants such as di-Na N-lauryl-$\beta$-iminodipropionate or lecithin;

anionic surfactants, such as Na lauryl sulphate, fatty alcohol ether sulphates, mono/dialkyl polyglycol ether orthophosphoric acid ester monoethanolamine salt; surfactants such as cetyltrimethylammonium chloride.

Other auxiliaries which may be mentioned are: substances increasing viscosity and stabilizing the emulsion such as carboxymethyl cellulose, methyl cellulose and other cellulose and starch derivatives, polyacrylates, alginates, gelatin, gum arabic, polyvinylpyrrolidone, polyvinyl alcohol, copolymers of methyl vinyl ether and maleic anhydride, polyethylene glycols, waxes, colloidal silica or mixtures of the substances mentioned.

Suspensions may be administered orally, dermally or as an injection. They are prepared by suspending the active compound in an excipient liquid, if appropriate with the addition of other auxiliaries such as wetting agents, colorants, absorption-promoting substances, preservatives, antioxidants and light screens.

Excipient liquids which may be mentioned are all homogeneous solvents and solvent mixtures.

Wetting agents (dispersants) which may be mentioned are the surfactants indicated above.

Other auxiliaries which may be mentioned are those indicated above.

Semi-solid preparations can be administered orally or dermally. They differ from the suspensions and emulsion above only by their higher viscosity.

In order to prepare solid preparations, the active compound is mixed with suitable excipients, if appropriate with the addition of auxiliaries, and brought into the desired form.

Excipients which may be mentioned are all physiologically tolerable solid inert substances. Those used are inorganic and organic substances. Inorganic substances are, for example, sodium chloride, carbonates such as calcium carbonate, hydrogencarbonates, aluminum oxides, silicic acids, aluminas, precipitated or colloidal silica and phosphates.

Organic substances are, for example, sugars, cellulose, foodstuffs and feeds such as powdered milk, animal meals, cereal meals and shreds, and starches.

Auxiliaries are preservatives, antioxidants and colorants which have already been mentioned above.

Other suitable auxiliaries are lubricants and glidants such as, for example, magnesium stearate, stearic acid, talc, bentonites, disintegration-promoting substances such as starch or crosslinked polyvinylpyrrolidone, binders such as, for example, starch, gelatin or linear polyvinylpyrrolidone and dry binders such as microcrystalline cellulose.

The active compounds may also be present in the preparations as a mixture with synergists or with other active compounds.

Ready-to-use preparations contain the active compound in concentrations of 10 ppm–20 percent by weight, preferably from 0.1–10 percent by weight.

Preparations which are diluted before use contain the active compound in concentrations of 0.5–90 percent by weight, preferably from 1 to 50 percent by weight.

In general, it has proved advantageous to administer amounts of about 0.5 to about 50 mg, preferably 1 to 20 mg, of active compound per kg of body weight per day to attain effective results.

The active compounds can also be administered together with the feed or drinking water of the animals.

Feeds and foodstuffs contain 0.01 to 100 ppm, preferably 0.5 to 50 ppm of the active compound in combination with a suitable edible material.

Such a feed and foodstuff can be used both for healing purposes and for prophylactic purposes.

The preparation of such a feed or foodstuff is carried out by mixing a concentrate or a premix which contains 0.5 to 30%, preferably 1 to 20% by weight, of an active compound in a mixture with an edible organic or inorganic excipient with customary feeds. Edible excipients are, for example, corn flour or corn and soy bean flour or mineral salts which preferably contain a small amount of an edible dust-preventing oil, for example corn oil or soy oil. The premix obtained in this way can then be added to the complete feed before feeding it to the animals.

Use in coccidiosis may be mentioned as an example:

For the curing and prophylaxis, for example, of coccidiosis in poultry, in particular in hens, ducks, geese and turkeys, 0.1 to 100 ppm, preferably 0.5 to 100 ppm, of an active compound are mixed with a suitable edible material, for example a nutritious feed. If desired, these amounts can be increased, particularly if the active compound is well tolerated by the recipient. Administration can appropriately be carried out via the drinking water.

For the treatment of individual animals, for example in the case of the treatment of coccidiosis in mammals or toxoplasmosis, preferably amounts of active compound of 0.5 to 100 mg/kg of body weight are administered daily in order to obtain the desired results. In spite of this, it may be periodically necessary to deviate from the amounts mentioned, in particular depending on the body weight of the test animal or the type of administration method, and also on account of the species of animal and its individual reaction to the active compound or the manner of formulation and the time or the interval at which it is administered. Thus, in certain cases it may be sufficient to manage with less than the minimum amount previously mentioned, whereas in other cases the upper limit mentioned must be exceeded. With the administration of larger amounts, it may be expedient to divide these into a number of individual administrations over the course of the day.

The compounds according to the invention are moreover active against various fish parasites including the helminths (worms).

The fish parasites include from. the sub-kingdom of the protozoa, species of the Ciliata phylum, for example *Ichthyop-hthirius multifiliis, Chilodonella cyprini*, Trichodina spp., Glossatella spp., Epistylis spp. of the Myxosporidia phylum, for example *Myxosoma cerebralis*, Myxidium spp., Myxobolus spp., Heneguya spp., Hoferellus spp., the Microsporidia class, for example Glugea spp., Thelohania spp., Pleistophora spp., from the flat helminths phylum: trematodes; Monogenea, for example Dactylogyrus spp., Gyrodactylus spp., Pseudodactylogyrus spp., Diplozoon spp., cestodes, for example from the Caryphyllidea groups (for example *Caryophyllaeus laticeps*), Pseudophyllidea (for example Diphyllobothrium spp.), Tetraphyllidea (for example Phyllobothrium spp.) and Protocephalida (for example species of the genus Proteocephalus) and from the Arthropoda phylum, various crustaceae, in particular from the sub-classes of the Branchiura (fish-lice) and Copepoda (copepods) and the orders of the Isopoda (isopods) and Amphipoda (amphipods).

The treatment of the fish is carried out either orally, for example via the feed or by short-term treatment, "medicinal bath", into which the fish are put and in which they are kept for some time (minutes up to a number of hours), for example when transferring from one breeding pond to another.

However, temporary or permanent treatment of the environment of the fish (for example entire pool units, aquaria, tanks or ponds), in which the fish are kept, can also be carried out.

The active compound is administered in preparations which are suited to the applications.

The concentration of the active compound in the preparations is 1 ppm to 10% by weight.

Preferred preparations for short-term treatment in the course of use as a "medicinal bath", for example in the treatment when transferring the fish or for the treatment of the environment (pool treatment) of the fish, are solutions of the active compound in one or more polar solvents which give an alkaline reaction on diluting with water.

For the preparation of these solutions, the active compound is dissolved in a polar, water-soluble solvent which either gives an alkaline reaction or to which is added an alkaline water-soluble substance. The latter is advantageously also dissolved in the solvent, but can also be suspended in the solvent and only dissolve in the water. After addition of the active compound solution, the water should have a pH of 7-10, but preferably a pH of 8-10.

The concentration of the active compound can be in the range from 0.5-50%, but preferably in a range from 1-25%.

Suitable solvents are all water-soluble solvents in which the active compound is soluble at a sufficient concentration and which are physiologically acceptable.

These are ethyl alcohol, isopropyl alcohol, benzyl alcohol, glycerol, propylene glycol, polyethylene glycols, poly(oxoethylene)-poly(oxypropylene) polymers, basic alcohols such as mono-, di- and triethanolamine, ketones such as acetone or methyl ethyl ketone, esters such as ethyl lactate, in addition N-methylpyrrolidone, dimethylacetamide, dimethylformamide, and in addition dispersants and emulsifiers such as polyoxyethylated castor oil, polyethylene glycol sorbitan monooleate, polyethylene glycol stearate or polyethylene glycol ethers and polyethylene glycol alkylamines.

Bases which may be mentioned for adjusting the alkaline pH are organic bases such as basic amino acids such as L-or D,L-arginine, L- or D,L-lysine, methylglucosamine, glucosamine, 2-amino-2-hydroxy-methylpropane-1,3-diol and in addition such as N,N,N',N'-tetrakis-(2-hydroxypr-opyl)ethylenediamine or polyether tetrol based on ethylenediamine (M.W. 480–420), inorganic bases, such as ammonia or sodium carbonate—if appropriate with the addition of water.

The preparations may also contain 0.1 to 20% by weight, preferably 0.1-10% by weight, of other formulation auxiliaries, such as antioxidants, surfactants, suspension stabilizers and thickeners such as, for example, methylcellulose, alginates, polysaccharides, galactomannans and colloidal silicic acid. The addition of colorants, flavoring and builders for animal nutrition is also possible. Even acids which, together with the base initially introduced, form a buffer system or reduce the pH of the solution, can be mentioned here.

The concentration of the active compound during use depends on the type and duration of the treatment, and the age and condition of the treated fish. It is, for example, for a short-term treatment, 2-50 mg of active compound per liter of water, preferably 5-10 mg per liter, for a treatment period of 3-4 hours. For the treatment of young carp, for example, a concentration of 5-10 mg/l and a treatment period of about 1-4 hours are used.

Eels are treated using concentrations of about 5 mg/l for about 4 hours.

For a relatively long treatment period or for continuous treatment, the concentration can be chosen to be correspondingly lower.

For pool treatments, 0.1-5 mg of active compound per liter of water can be used.

Preparations for use as a food additive are, for example, composed as follows:

| a) | Active compound of the formula I | 1-10 parts by weight |
| | Soy bean protein | 49-90 parts by weight |
| b) | Active compound of the formula I | 0.5-10 parts by weight |
| | Benzyl alcohol | 0.08-1.4 parts by weight |
| | Hydroxypropyl-methyl cellulose | 0-3.5 parts by weight |
| | Water | remainder to 100 |

Preparations for use in "medical baths" and for pool treatment are, for example, composed and prepared as follows.

| c) | 2.5 g | of active compound of the formula (I) are dissolved in 100 ml of triethanolamine with warming. |
| d) | 2.5 g | of active compound of the formula (I) |
| | 12.5 g | of lactic acid are dissolved in 100 ml of triethanolamine with warming and stirring. |
| e) | 10.0 g | of active compound of the formula (I) is dissolved in 100 ml of monoethanolamine. |
| f) | Active compound of the formula I | 5.0 g |
| | Propylene glycol | 50.0 g |
| | Sodium carbonate | 5.0 g |
| | Water | to 100 ml |
| g) | Active compound of the formula I | 5.0 g |
| | Monoethanolamine | 10 g |
| | N-Methylpyrrolidone | to 100 ml |
| h) | Active compound of the formula I | 2.5 g |
| | Sodium carbonate | 5.0 g |
| | Polyethylene glycol 200 | to 100 ml |

The active compound is dissolved in polyethylene glycol with warming and sodium carbonate is suspended therein.

EXAMPLE A

Coccidiosis in Chickens

Chicks 9 to 11 days old were infected with 40,000 sporulated oocysts of strongly virulent strains of *Eimeria acervulina, E. maxima* and *E. tenella,* the causative organisms of intestinal coccidiosis.

From 3 days before infection until 8 days after infection (end of the test), the active compound was administered mixed into the feed of the animals in the concentration indicated.

The number of oocysts in the faeces was determined with the aid of the McMaster chamber (see Engelbrecht and coworkers "Parasitologische Arbeitsmehoden in Medizin und Veterinärmedizin" [Parasitological Working Methods in Medicine and Veterinary Medicine], p. 172, Akademie-Verlag, Berlin (1965)).

Those doses are regarded as effective which prevented completely or to a large extent the shedding of oocysts and/or clinical symptoms of coccidiosis including mortality. The effective doses are indicated in the following table:

TABLE 1

| | | | Coccidiosis in chickens | | |
| Example No. | Dose ppm. | Death rate dead/employed | Oocyst excretion in % in comparison to untreated infected control | Weight increase in % in comparison to uninfected untreated control | Blood excretion with the faeces |
| --- | --- | --- | --- | --- | --- |
| untreated infected control | | 2/9 | 100 | 40 | heavy |
| 9 | 50 | 0/3 | 0 | 100 | none |
| | 25 | 0/3 | 0 | 100 | none |
| | 10 | 0/3 | 0.3 | 100 | none |

EXAMPLE B

*Eimeria faloiformis*/Mouse Test

Laboratory mice of about 18 g body weight are infected artificially with about 18,000 sporulated oocysts of Eimeria falciformis per animal. The infected animals are then treated on the 1st, 2nd, 3rd, 6th, 7th and 8th day after the infection.

0.5 ml of water in which the indicated dose of active compound is dissolved or suspended is administered to each animal via a stomach tube. 4 animals are treated per dose. 9 days after infection in the intestine, clinical symptoms are observed and mortality during the test are used to evaluate the activity. The degree of activity is evaluated as follows:

highly effective=2
slightly effective=1
inactive=0

Control: in the untreated control animals, severe excretion, bloodstained diarrhoea and a mortality due to infection of about 30% of the animals occur on the 7th day after infection.

TABLE 2

| Active compound Example No. | Dose mg/kg of body weight | Activity after 9 days |
| --- | --- | --- |
| Control | — | 0 |
| 9 | 50 | 2 |
| | 10 | 2 |
| | 5 | 2 |
| | 50 | 2 |
| | 10 | 2 |
| 12 | 5 | 2 |
| | 1 | 2 |
| | 0.5 | 2 |

The following are prepared analogously:

EXAMPLE 1

2-[4-(2-Pyridyloxy)phenyl]-4-N-methyl-3,5-(2H,4H)-dioxo-1,2,4-triazine

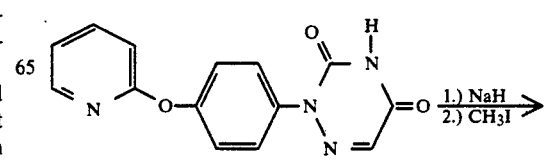

-continued

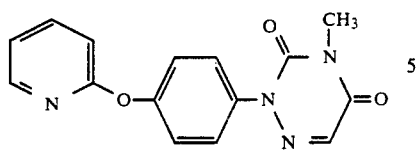

2 g (7 mmol) of pyridinyloxyarylazauracil are dissolved in 20 ml of absolute DMSO and 0.16 g (6 mmol) of sodium hydride is added. The mixture is stirred at RT for 20 min and 1.5 g (9 mmol) of methyl iodide in 5 ml of DMSO are then added under argon. The mixture is heated to 50° C. and kept at this temperature for 3 h. The reduction mixture is subsequently concentrated in vacuo and water is then added. After filtering off the precipitated solid with suction, 1.5 g (72% of theory) of the N-methyl compound are thus obtained.

EXAMPLE 2

2-(2-Pyridyloxyhenyl)-1,2,4-triazine-3,5(2,4H)dione

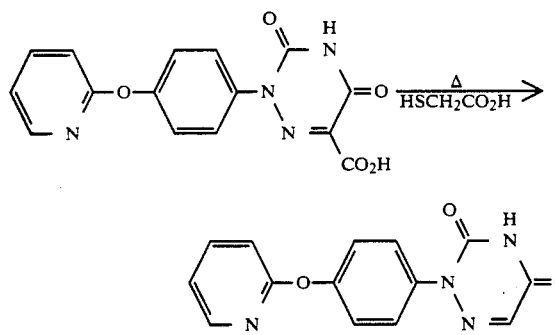

10 g (0.03 mol) of the illustrated carboxylic acid are heated to 170° C in 20 ml of mercaptoacetic acid. After 1.5 h, the mixture is allowed to cool, water is added and 27 g (82% of theory) of the illustrated decarboxylated product are obtained after filtering off.

EXAMPLE 2a 2-(4-(2-Pyridinyloxy)-3,5-(2H,4H)dioxo-6-cyano-1,2,4triazine

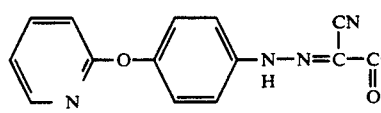

12 g (0.034 mol) of hydrazonocyanourethane and 1.8 g (0.44 mol) of NaOH are heated under reflux in 50 ml of abs. ethanol for 2 h. The mixture is subsequently cooled, acidified with hydrochloric acid and concentrated in vacuo. The residue is stirred with water and the precipitate deposited is filtered off with suction. After drying, 8.9 g (85% of theory) of cyanaozauracil are thus obtained from which the corresponding azauracilcarboxylic acid is formed by hydrolysis.

EXAMPLE 3

1-[3,5-Dichloro-4-(2-pyridinyloxy)-phenyl]-1,2,4-triazine-3,5(2H,4H)-dione

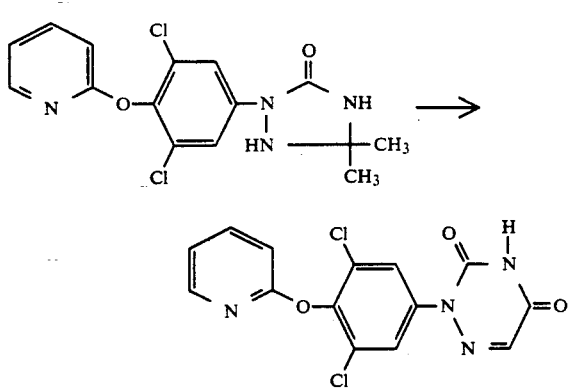

3 g (8.5 mmol) of 1-[3,5-dichloro-4-(2-pyridinyloxy)-phenyl-]3,3-dimethyl-1,2,4-triazolidin-5-one are dissolved in 50 ml of dioxane and 0.78 g (8.5 mmol) of glyoxylic acid monohydrate and 0.1 ml of conc. HzSO are added. The mixture is initially stirred at room temperature for 2 h and then a further 0.8 g of glyoxylic acid is added. After stirring under reflux for 5 h, the reaction mixture is poured into water and extracted 3×with ethyl acetate. The solvent is stripped off in vacuo and the residue is chromatographed on SiOz using dichloromethane/methanol (95:5). 1.2 g (40% of theory) of the corresponding azauracil are thus obtained.

EXAMPLE 4

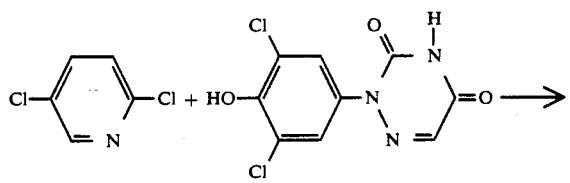

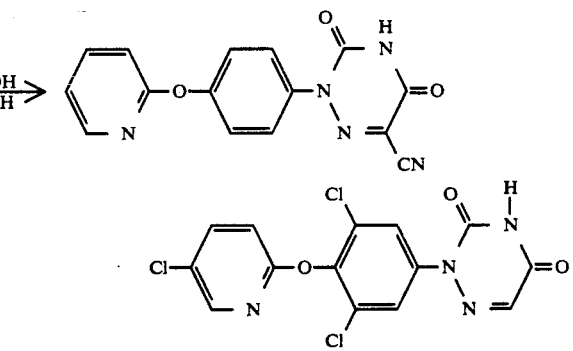

29 g (0.01 mol) of dichloro-hydroxyphenylazauracil, 1.2 g (0.01 mol) of dichloropyridine and 1.4 g (0.01 mol) of potassium carbonate are stirred under reflux in 20 ml of dry DMF for 2 h. The cooled reaction mixture is acidified with HCl and the product deposited is filtered off with suction. After recrystallizing from ethanol, 2.9 g (78% of theory) of the illustrated pyridinyloxyarylazauracil are obtained.

The following can be prepared by analogous methods:

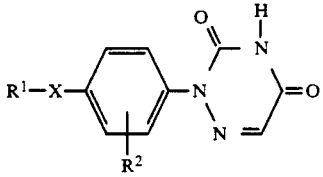

| Ex. No. | R¹ | X | R² | M.p. [°C.] |
|---|---|---|---|---|
| 5 | O₂N-(pyridyl) | O | H | 262 |
| 6 | H₃CS-(pyrimidinyl-methyl) | O | H | 168 |
| 7 | NO₂, Cl-pyridyl | O | 3,5-Cl₂ | 231 |
| 8 | H₃CS-(pyrimidinyl-methyl) | O | 3,5-Cl₂ | 185 |
| 9 | F₃C-pyridyl | O | 3,5-Cl₂ | 191 |
| 10 | CF₃, Cl, Cl-pyrimidinyl | O | 3,5-Cl₂ | 201 |
| 11 | O₂N-pyridyl | O | 3,5-Cl₂ | 221 |
| 12 | NO₂-pyridyl | O | 3,5-Cl₂ | 205 |
| 13 | Cl, F₃C-pyridyl | O | 3,5-Cl₂ | 208 |

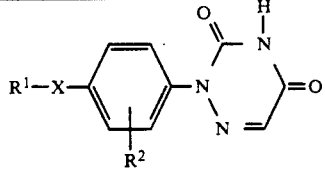

| Ex. No. | R¹ | X | R² | M.p. [°C.] |
|---|---|---|---|---|
| 14 | 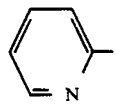 | O | 3,5-Cl₂ | 223 |

It will be appreciated that the instant specification is set forth by way of illustration and not limitation, and that various modifications and changes may be made without departing from the spirit and scope of the present invention.

What is claimed is:

1. A method of combating parasitic protozoa which comprises applying thereto a parasiticidally effective amount of a 1,2,4-triazinedione of the formula:

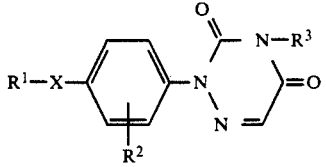

in which
X represents O, S, SO₂, SO or —CR⁴(CN)—, R⁴ represents hydrogen or alkyl,
R¹ represents pridyl or pridyl substituted by C₁₋₄-alkyl, C₁₋₄-halogenoalkyl, halogen, nitro, CN, C₁₋₄-alkoxy, C₁₋₄-halogenoalkoxy, C₁₋₄-alkylthio, C₁₋₄-halogenoalkylthio, C₁₋₄-halogenoalysulphonyl, C₁₋₄-halogenoalkysulphinyl, amino, C₁₋₄-alkylamino, C₁₋₄-halogenoalkylamino or acylamino,
R² represents one or more radicals selected from the group consisting of hydrogen, halogen, C₁₋₄-alkyl and 1-5-halogeno(C₁₋₄)-alkyl, and
R³ represents hydrogen or methyl.

2. The method according to claim 1, in which
X represents O or CH(CN),
R¹ represents pyridyl or pyridyl substituted by nitro, chlorine, methyl or trifluoromethyl,
R² represents one or more radicals selected from the group consisting of hydrogen, methyl and chlorine, and
R³ represents hydrogen or methyl.

3. The method according to claim 1, wherein such compound is 1-[3,5-dichloro-4-(5-trifluoromethyl-2-pyridinyloxy)-phenyl]-1,2,4-triazine-3,5-(2H,4H,)-dione of the formula

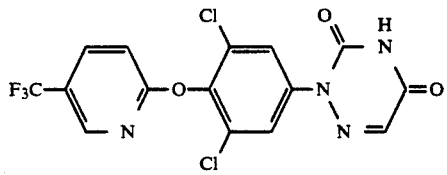

4. The method according to claim 1, wherein such compound is 1-[3,5-dichloro-4-(3-nitro-2-pyridinyloxy)-phenyl]-1,2,4-triazine-3,5-(2H,4H)-dione of the formula

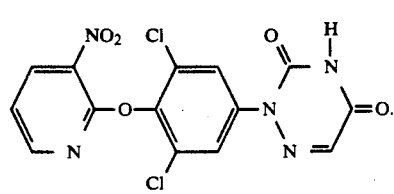

* * * * *